United States Patent [19]

Hustede et al.

[11] 3,941,656

[45] Mar. 2, 1976

[54] MANUFACTURE OF CITRIC ACID BY SUBMERGED FERMENTATION

[75] Inventors: Helmut Hustede, Ladenburg (Neckar), Germany; Hermann Rudy, deceased, late of Heidelberg, Germany; by Liselotte Rudy, nee Ringelmann, heir; by Hans Rudy, heir, both of Heidelberg, Germany; by Barbara Sallewsky, nee Rudy, heir, St. Herman, Canada

[73] Assignee: Joh. A. Benckiser GmbH, Ludwigshafen (Rhine), Germany

[22] Filed: Nov. 2, 1971

[21] Appl. No.: 195,007

[52] U.S. Cl............................................... 195/36 R
[51] Int. Cl............................................ C12d 1/04
[58] Field of Search........................... 195/36 R, 47

[56] References Cited
UNITED STATES PATENTS 3,118,821  1/1964  Clark .............................. 195/36 R

*Primary Examiner*—Alvin E. Tanenholtz
*Attorney, Agent, or Firm*—Weiser, Stapler & Spivak

[57] ABSTRACT

The invention concerns a process for producing citric acid during which ferri- or ferrocyanide ions like potassium ferrocyanide are added at a particular time and in a preselected amount.

22 Claims, No Drawings

MANUFACTURE OF CITRIC ACID BY SUBMERGED FERMENTATION

This invention deals with a process for making citric acid by submerged fermentation under aerobic conditions in sugar-containing or other carbohydrate fermentable substrates, in particular substrates of sugar cane or sugar beet molasses. More particularly the invention deals with a process involving addition of specific amounts of ferri- or ferrocyanide ions, especially potassium ferrocyanide, at specified times.

The prior art has described the addition of potassium ferrocyanide to surface and submerged fermentations with sugar cane or sugar beet molasses. There are extensive publications showing that the effect of the potassium ferrocyanide in the treatment of the molasses appears to be predicated on its property to form substantially insoluble complexes with a large number of cations, and thereby to effectuate the removal of assimilable heavy metals (particularly iron) which when present even in small amounts cause undesirable filamentous growth of the microorganism. There is also some indication that the ferrocyanide has a toxic action on the mold itself which favorably affects citric acid production. Usually, an aqueous solution of the ferrocyanide is added to the dilute molasses in conjunction with heat treatment, usually above 80°C. In this manner the concentration of the undesirable trace metals in the molasses is decreased.

It has further been disclosed that the amount of potassium ferrocyanide can influence the production of citric acid significantly, and that citric acid production is decreased when high amounts of potassium ferrocyanide are added to the medium after inoculation. Likewise, a similar adverse effect on the yield of citric acid is obtained when large amounts of potassium ferrocyanide are added to the fermentation medium before its sterilization. In practice, because of the variations in the composition of the molasses, the problems of controlling the conditions of the fermentation are aggravated.

Apparently, there is such a delicate and unpredictable relationship between the effect of the timing of addition and amounts of ferrocyanide and yields of citric acid that, notwithstanding various attempts at solving this problem, these difficulties have not yet been overcome. As a result, yields of citric acid are still obtained which are far from optimum. It has now been discovered that such adverse effects on the production of citric acid can be overcome in accordance with the process of the invention.

The process of the invention involves a recognition of the potential role and of the use of the buffering capacity of the molasses with respect to ferro- or ferricyanide ions and the complexing property of the ferro- or ferricyanide, in particular potassium ferrocyanide, with respect to certain metals. Generically ferro- and ferricyanide ions will be referred to as ferrocyanide herein. It has now been recognized that while the complexing property of the ferrocyanide is limited to its ability to tie up certain metals, as described above, its buffering capacity includes the complexing property with respect to the metals, and also its reactiveness with other substances and compounds in the molasses. Further, the cyanide ions act, in certain amounts as a toxin for the enzymes of the respiratory cycle of the fungi. The ferrocyanide buffer capacity is thus an integral entity which is part of the fermentation system as a whole and includes, in accordance with this invention, the metal complexing property. Unless the molasses contain only complexable metals and no other substances that can be bound by the ferrocyanide ions, the amount of ferrocyanide ions necessary to form a complex by tying up the metals, like the heavy metals, is smaller than the total amount of ferrocyanide necessary to bind the other substances in the medium and also for a complex of the metals.

A distinctive aspect of the process comprises maintaining in the medium complex-forming sites available for buffering the potassium ferrocyanide as it dissociates during the fermentation. In this manner, the concentrated effect of the cyanide as enzyme poison is limited. The process further comprises having continuously present an excess of cyanide ions over the amount required for metal complex-forming. During the fermentation, an appreciable amount of free ferrocyanide is thus still buffered by the whole buffering capacity of the system. The process of the invention is further described hereinafter.

The process of the invention comprises adding ferri- or ferrocyanide ions to the main fermentation medium during the course of the fermentation in several steps. Further, the invention comprises adding a specified amount of potassium ferrocyanide before i.e. up to the time of but not later than sterilization of the fermentation medium and adding a second specified amount after its sterilization. In one embodiment, the second amount is all added before the inoculation; in another embodiment the second amount is added after inoculation during the course of the fermentation. In yet another embodiment, the second amount is added partially, i.e., about half thereof before, and the remainder after inoculation. All amounts in the specified portions, can be added incrementally.

In accordance with the invention, a highly selective and controlled addition of ferrocyanide ions is carried out both in terms of timing of addition and in amounts used. In the process, the ferrocyanide ions which are added before, or at the latest during or in conjunction with sterilization, is so controlled that less than all of the assimilable heavy metals are complexed or sequestered with the ferrocyanide ion. The medium thus retains a residual buffering capacity and complexing property which is available for further additions of ferrocyanide ions. The process therefore provides for a continuous and gradual decrease of the complexing capacity of the medium and the gradual complexing of ferrocyanide ions during the fermentation of the carbohydrate, e.g., sugar to citric acid. In one aspect of the invention about 25 to 50% of the necessary total amount of potassium ferrocyanide ions are added prior to sterilization of the medium and the remainder or about 75 to 50% is added after sterilization thereof. In a special and advantageous embodiment of the invention, the ferrocyanide ions are added in the second step after inoculation incrementally or continuously during the process of the main fermentation. The selective addition of ferrocyanide ions in accordance with the invention before and after sterilization and inoculation causes unexpectedly a most efficient production of citric acid in a remarkably high yield. In the process of the invention potassium ferrocyanide is preferred.

In another highly advantageous embodiment, it has been found that the potassium ferrocyanide added in the first step, before or at the time of sterilization shall be adjusted in such an amount that after the sterilization and the addition of the remainder only about one-third to two-thirds or 33.3 to 66.6% of the total amount of ferrocyanide are bound by complexing the metals. In this manner about two-thirds to one-third of the total ferrocyanide to be used is still available for complexing with the residual buffering capacity of the system. The residual complexing capacity of the medium is thus available for free ferrocyanide ions that may become available as a result of an increasingly more acidic pH during the fermentation. In this manner of practicing the invention, there is provided already from the beginning to the end of the fermentation a continuous utilization of ferrocyanide. Thus, the amount of excess free cyanide ions present is so combined, or complexed, that the enzymes of the respiratory chain are left unblocked. Accordingly, the fermentation curve remains constant from the beginning to the end, and as a result, the conversion of sugar to citric acid reaches over 100%, i.e., the conversion rate approaching or even exceeding the theoretical amount.

In accordance with the invention, there is used, at the time specified, the ferro- or ferricyanide ion as a suitable salt, preferably a water-soluble salt, such as an alkali metal salt. The salt should be capable of liberating ferro- or ferricyanide ions under the process conditions. At the present potassium ferrocyanide is preferred. The amount of salt to be used in the practice of the invention is based on potassium ferrocyanide. For ready conversion to ferro- or ferricyanide ion, the amounts given for the potassium salt can be divided by two. The amount of ferrocyanide or ferricyanide ions to be used is therefore 0.25 to 1.5, preferably 0.025 to 0.15 gram per liter.

The necessary amount of ferrocyanide to be used depends on the composition of molasses. The composition of the molasses is determined by a preliminary laboratory test simulating sterilization conditions, wherein suitable samples of molasses containing varying amounts of ferrocyanide ions, e.g., potassium ferrocyanide are heated to 100°C. for half an hour and then cooled to 20°C. A heavy precipitate settles out. The amount of potassium ferrocyanide is then determined in the respective samples. From that data, the amount of ferrocyanide ions as potassium ferrocyanide, for example, to be consumed or complexed, i.e., the complexing capacity of the molasses depending on the composition of the molasses, is determined for the subsequent fermentation in such a manner that there is still available a reactant for the potassium ferrocyanide, i.e., that the fermentation medium retains a potassium ferrocyanide buffering capacity.

The total amount of potassium ferrocyanide to be added to the medium may range from about 0.2 to 3 gram or often 0.8 to 1.5 gram per liter, depending on the particular content of heavy metals of the molasses. Under certain circumstances because of the properties of the molasses or the particular carbohydrate-containing substrate selected, broader ranges of potassium ranging from about 0.05 to 4 gram per liter of medium.

The selective addition of ferrocyanide ions before and after sterilization shows remarkable advantages over the conventional process in the fermentation of rawsugar molasses such as, for instance, blackstrap, beet, cane or citrus molasses, whereby the necessary amount of potassium ferrocyanide is added before and after sterilization, and/or after inoculation. The advantages of the process of the invention are also independent from the manner of growing the microorganism inoculum for the fermentation, or the particular amounts of ferrocyanide used so long as they are related, as specified, to the buffering capacity of the medium.

The selective addition of the ferrocyanide in the amount relative to the buffering capacity of the medium of the invention can be carried out in known citric acid-producing fermentation processes.

In the process of the invention, there may be used any of the citric acid producing microorganisms such as the genera Aspergillus, Penicillium or Mucor. Examples of useful species of these genera are *A. niger*, *A. Wentii*, *A. clavatus*, *P. Citrinum*, *Mucor Piriformis* and *Trichoderma viride* (ATCC No. 1323). The species which has been found most useful is *A. niger*. Among these such strains at ATCC 10577, ATCC 1015 or Wisconsin 72-4, also named N.R.C.A. -1-233 (National Research Council Publication No. 2359), and mutants thereof are quite suitable. Others are disclosed in the scientific literature. Suitable microorganisms which produce citric acid are on deposit in recognized depositories like American Type Culture Collection, Washington, D.C. (ATCC), Headquarters Quartermaster Research and Development Command, Quartermaster Research and Development Center, U.S. Army (QM), Northern Regional Research Laboratory of the Department of Agriculture, Peoria (NRRI), Nagoa Institute, Tokyo (NI), Institute of Fermentation, Osaka (IFO), National Hygienic Laboratory, Tokyo (NHL) and Kyowa Hakko Kogyo Co., Ltd. (Kyowa).

In the process of the invention, it is advisable to use as inoculum pellets of the fungi, for instance pellets of a strain *Aspergillus niger*. Preparation of such pellets is known, as for example shown by Martin in U.S. Pat. No. 2,739,923 or Fried et al. in U.S. Pat. No. 2,910,409. If desired suitable pellets may also be obtained by treating spores of a suitable citric acid-producing microorganism, e.g., an Aspergillus or Penicillium with potassium ferrocyanide during the intensive physiological development period which occurs during the transition period ranging from the spore-swelling stage to the spore-germination stage. Such special pellets are identified by the substantial absence of an adaptation lag, as evidenced for instance by the pH curves, when transferred from a inoculum growth medium to a typical fermentation medium for citric acid-producing microorganisms and for their ability to produce citric acid at a substantially constant rate through the fermentation. Such method for making pellets is disclosed in copending application filed on even date and entitled PRODUCTION OF CITRIC ACID BY SUBMERGED FERMENTATION.

The fermentation medium may contain any carbohydrate source which can be converted to citric acid by the microorganism, like sugar from conventional crude sugar sources, as sugar beet, sugar cane, molasses or citrus molasses or other carbohydrates and suitable nutrient salts such as, for instance, phosphates, nitrates, and so on in suitable amounts as is known from the prior art such as from U.S. Pats. No. 2,739,923; 2,970,084; 2,910,409; 2,492,673; 2,492,667; 2,400,143; 2,394,031, Belgian patent No. 596,964 and others.

The diluted molasses mash is preferably sterilized before preparing the inoculum or the bulk fermentation medium. By sterilization is meant treatment in which all or substantially all of the undesirable microorganisms are destroyed, but some harmless ones may remain viable.

Other conditions of growth of the microorganisms, other treatment of the molasses, the handling of the inoculum and other conditions of the fermentation are known from U.S. Pats. Nos. 2,674,561; 2,970,084; 2,910,409; 2,739,923; 2,492,673; 2,492,667; 2,400,143; 2,394,031; 2,883,329; 2,739,923, particularly columns 2, 3 and 4 thereof; 3,105,015; 3,118,821; and Belgian patent No. 506,964, which are incorporated herein by reference.

The measurement of the residual ferrocyanide ion concentration was carried out by the method of Marier and Clark -- "The Analyst," J. Soc. Anal. Chem., vol. 85, No. 1013, pp. 574–579 (1960). The accuracy of this method is ±3 V/ml.

The yield of citric acid is determined as percent citric acid (wt./vol. of medium) or percent conversion of available sugar (wt./wt.).

The following working examples are provided as an illustration of the preferred embodiments of the invention but are not to be construed as a limitation thereto.

EXAMPLE 1

In a fermentation vessel, 320 liters of fermentation medium of blackstrap molasses are diluted with tap water to approximately 115% by weight sugar. There are added to the medium from the beginning 80 grams of monoammonium dihydrogen monophosphate and the pH value is adjusted to 5. The medium is sterilized by heating at about 100°C. for half an hour. Aeration through a sparger is provided at a rate of 6 to 8 cubic meters of air per hour which is distributed with a stirrer rotating at 300 r.p.m. The temperature is adjusted to about 32°C. and the medium is inoculated with spores ($4 \times 10^{10}$) of Aspergillus niger. Eight hours after the inoculation, there are added 430 grams of potassium ferrocyanide. After a total of about 18 to 19 hours, there is formed under these conditions from each spore a long mycelium of a length of about 0.04 to 0.07 mm, which is thickened, globular and branched in a cauliflower-like manner at each end. The mycelium develops during an additional 5 hours with a strong pH drop into pellets which have an average diameter of about 0.2 mm. When the pH drops to about 4.3, the inoculum is ready for use in the main fermentation.

A fermentation medium, 2.4 cubic meter, is prepared in a suitable fermentation vessel from blackstrap molasses by diluting to approximately 15% by weight sugar with tap water and the pH is adjusted to about 5. The medium to which there is added 1500 grams of potassium ferrocyanide is then sterilized at 100°C. for half an hour. In preliminary tests, the buffer capacity to potassium ferrocyanide of the molasses was determined to be relatively high; the amount to be added here corresponds to about 55% to 60% of the amount that would be required for complete complexing of the metals in the molasses. After allowing the fermentation medium to cool to the fermentation temperature of about 28° to 32°C., there is made a further addition of 2400 grams of potassium ferrocyanide. The medium is aerated for a few minutes through an air sparger at a rate of 0.2 volume of air per volume of medium per minute, this being equivalent to an air rate of about 35 to 40 cubic meters per hour while agitation is provided with a stirrer rotating at 100 r.p.m. to distribute the air thoroughly through the medium.

The medium is then inoculated with the pellet inoculum of A. niger as prepared above.

After inoculation, the pH of the medium which dropped as a result of the acidity of the inoculum is determined. Three hours later, as a result of the continuous production of citric acid from the pellet mycelium, it has already dropped further by 0.1 to 0.2 pH units. After 18 hours of fermentation there are added about 750 grams of ammonium nitrate and the concentration of potassium ferrocyanide is determined after 40 hours of fermentation. When the concentration of potassium ferrocyanide is found to be below 0.3 per liter, it is then raised by further addition of potassium ferrocyanide to at least 0.4 gram per liter. In this manner, the concentration of potassium ferrocyanide is maintained until the end of the fermentation, there are again added 750 grams of ammonium nitrate. After three and a half days, the fermentation is terminated. The fermentation medium contains 13.2% citric acid, a yield of 89% based on the initial amount of sugar available.

EXAMPLE 2

In a comparative experiment, the amounts of potassium ferrocyanide used prior to sterilization and after are reversed. There are added first 2400 grams per liter and then after sterilization 1500 grams per liter of potassium ferrocyanide. The fermentation is below a pH of 2.9 and is slowed down. The yield of citric acid is reduced by about 30 to 35% based on the initial sugar present.

EXAMPLE 3

The procedure of Example 1 is followed except that the 2400 grams of potassium ferrocyanide are added continuously during the course of the fermentation in such a manner that the concentration of potassium ferrocyanide is maintained through the fermentation at a minimum of at least about 0.3 gram per liter. After four and a half days the fermentation is terminated. The fermentation medium contains 12% of citric acid. This amounts to a yield of 80% based on the initial amount of sugar.

EXAMPLE 4

The procedure of Example 1 is repeated except that the 2400 grams of potassium ferrocyanide are added incrementally in 10 portions during the entire course of the fermentation. Equally high yield is obtained after four and a half days of fermentation.

EXAMPLE 5

In a fermentation vessel, sugar beet molasses is diluted to approximately 12% sugar by weight with tap water to obtain 320 liter of medium. There are added to the mash 80 grams of monoammoniumdihydrogen monophosphate. The pH is adjusted with sulfuric acid to 5.4 and the medium is sterilized at 100°C. for 35 minutes. The medium is aerated through a sparger so that a total of 6 to 8 cubic meters of air are provided while stirring at a rate of 300 r.p.m. to distribute the air thoroughly. The medium is then inoculated with Aspergillus niger spores (strain ATCC 10577) in an amount of $4 \times 10^{10}$ at a temperature of 32°C. after 6 hours of inoculation there are added 480 grams of potassium ferrocyanide. After a total of 14 to 15 hours there is formed under these conditions a mycelium of a length of about 0.04 to 0.07 mm. from each spore. The mycelium has a bulbous, swollen appearance and is cauliflower-like branched at each end. These short hyphae develop in an additional 3 to 4 hours into pellets having an average diameter of about 02. mm. During this intensive growth stage, the pH rises to about 6.0. Following this, a strong acid formation takes place. During this development phase the pH drops rapidly within 2 hours by about 1.5 to 2.0 pH units. When a pH value of about 4.6 is reached the inoculum is ready for inoculating the main fermentation medium. The inoculum contains from about 5 to 10% mycelium. The preparation of the inoculum takes about 20 hours.

In a suitable fermentation vessel, sugar beet molasses is diluted to approximately 15% by weight sugar with tap water to give a total of 2400 liter of fermentation medium. The pH buffering capacity of such beet molasses being very high, it is desirable to lower it by lowering the pH to about 5.5 with a suitable acid like a mineral and, like sulfuric acid. The solution or mash is therefore adjusted to a pH of about 5.5 with sulfuric acid. The mash is then sterilized for half an hour at 100°C. with addition of 900 grams of potassium ferrocyanide, then allowed to cool to the fermentation temperature of about 28° to 32°C. and there is added an additional amount of 1800 grams of potassium ferrocyanide. The medium is then aerated through an air sparger for a few minutes at a rate of 0.2 volume of air per volume of medium per minute which is equivalent to 40 cubic meters per hour. Agitation is provided with a stirrer rotating at 100 r.p.m. for thorough distribution of the air throughout the medium.

The medium is then inoculated with the pellets obtained as described above. After inoculation, the pH of the medium which has dropped as a result of the inoculum, is again determined. The intensive formation of acid which had started in the inoculum is slowed down. The pH drops by about one unit within 6 to 10 hours, depending on the buffer capacity of the molasses used. When the pH reaches about 5 (which usually occurs in about 4 to 7 hours) the fermentation temperature is lowered to 29°C. The intensive acid formation which had already started in the inoculum continues in the main fermentation. During this intensive citric acidproducing stage there occurs an active growth. This growth is promoted by the high buffering capacity of the sugar beet molasses, with an optimum growth in the pH range of about 3.5 to 3. In order to discontinue this intensive development phase after the fermentation medium has reached a pH of about 4.5 (this occurring in about 5 to 8 hours) and after the formation of about 8 to 10% mycelium, the buffering capacity of the fermentation medium is disrupted by the addition of sulfuric acid. Sulfuric acid is added within one hour in an amount sufficient to reach a pH of about 3.0 to 2.9. At the same time there are added 1800 grams of potassium ferrocyanide. In this manner it is noted that the intensive growth stage development is slowed down while the citric acid formation continues. After 20 hours of fermentation there are added 750 grams of ammonium dihydrogen monophosphate. If the concentration of ferrocyanide ions drops below 0.5 gram per liter, it is raised to 0.6 gram per liter. During the fermentation the potassium ferrocyanide concentration is thereby maintained at at least 0.4 gram per liter, or higher.

After five days the fermentation is terminated. The medium contains 12.4% of citric acid corresponding to a yield of 83% based on the amount of sugar initially used.

EXAMPLE 6

In the fermentation vessel of about 3000 liters there is prepared a fermentation medium of 2400 liters which is made up in part of blackstrap molasses and the remainder with a sugar solution (prepared from crystallized sugar). The blackstrap molasses and the sugar mixed in such proportion so that about 60% of the total sugar content is due to the sugar solution that is from the crystallized sugar and about 40% from the blackstrap molasses. The medium is diluted with tap water to a final concentration of about 15% sugar. To the fermentation medium there are then added 800 grams of potassium ferrocyanide and the pH is then adjusted by addition of sulfuric acid to about 5.0. The medium is then sterilized by heating for about half an hour at 100°C. After cooling to about 28° to 32°C. there is once more added potassium ferrocyanide in an amount of 1200 grams. The medium is then aerated as described in Example 1 and inoculated with pellets as prepared therein.

After 3 or 4 hours of fermentation there are added 600 grams of ammonium nitrate and 600 grams of ammonium dihydrogen phosphate to the medium. After further additions of potassium ferrocyanide and ammonium nitrate which are carried out during the fermentation following the procedure of Example 1, the fermentation is terminated in about 3½ days. There is obtained a fermentation medium which has a content of citric acid of about 13.1%. The yield based on the initial sugar is 87%.

We claim:

1. In the process of producing citric acid by submerged aerobic fermentation with a citric acid-producing microorganism in a sterilized carbohydrate-containing growth medium containing complexable substances and assimilable heavy metals, the improvement which comprises adding to the medium not later than its sterilization, a first amount of ferrocyanide ions in an amount necessary to complex only one-third to two-thirds of the total amount of complexable substances and assimilable heavy metals of the medium, and adding to the medium after sterilization of the medium an additional amount of ferrocyanide ions in an excess over the amount sufficient to complex the remaining assimilable heavy metals and the buffering capacity of the medium but said excess amount being insufficient to block the respiratory system of the microorganism.

2. The process of claim 1 wherein the first amount of ferrocyanide ions added is about 25 to about 50% of the total amount of ferrocyanide ions necessary to complex the complexable substances and assimilable heavy metals of the medium.

3. The process of claim 1 wherein the medium is a molasses-containing medium.

4. The process of claim 1 wherein the additional amount of ferrocyanide ions is added to the sterilized medium prior to its inoculation.

5. The process of claim 1 in which the ferrocyanide ions which are added during the fermentation are added continuously.

6. The process of claim 1 in which about one-half of the additional amount of ferrocyanide ions are added after sterilization and before inoculation and the remainder one-half is added after inoculation.

7. The process of claim 1 wherein the additional amount of ferrocyanide ions are added to maintain a level of at least about 0.4 gram per liter during the fermentation.

8. The process of claim 3 wherein the medium is sugar beet molasses.

9. The process of claim 1 wherein the ferrocyanide ions are provided as potassium ferrocyanide.

10. The process of claim 2 wherein the amount of ferrocyanide ions added during the fermentation are from 75 to about 50% of the total amount of ferrocyanide ions necessary to complex the complexable substances and assimilable heavy metals of the medium.

11. The process of claim 9 in which the total amount of potassium ferrocyanide added is in the range of about 0.05 to 4 grams per liter.

12. The process of claim 3 wherein the ferrocyanide ions which are made available during the fermentation due to increasing acidic conditions complex with and satisfy the residual buffering capacity of the molasses.

13. The process of claim 3 wherein the ferrocyanide ions are added continuously during the fermentation in an amount and rate sufficient to satisfy the residual buffering capacity of the molasses.

14. The process of claim 1 wherein the microorganism is an Aspergillus.

15. The process of claim 14 wherein there are used pellets of Aspergillus.

16. The process of claim 15 wherein the pellets are of *Aspergillus niger*.

17. The process of claim 3 wherein the medium is sugar beet molasses.

18. The process of claim 3 in which the medium is blackstrap molasses.

19. The process of claim 3 in which the medium is a mixture of molasses and sugar.

20. The process of claim 1 wherein the first amount of ferrocyanide ions is added prior to sterilization of the medium.

21. The process of claim 1 wherein said additional amount of ferrocyanide ions is added to the sterilized medium prior to its inoculation.

22. The process of claim 21 wherein said additional amount of ferrocyanide ions are added to the sterilized medium after its inoculation.

* * * * *